US009526423B2

(12) United States Patent
Edelman

(10) Patent No.: US 9,526,423 B2
(45) Date of Patent: Dec. 27, 2016

(54) METHOD FOR NON-CONTRAST ENHANCED MAGNETIC RESONANCE ANGIOGRAPHY

(71) Applicant: GHOST MEDICAL TECHNOLOGIES, LTD, Highland Park, IL (US)

(72) Inventor: Robert Edelman, Highland Park, IL (US)

(73) Assignee: Ghost Medical Technologies, Ltd., Highland Park, IL (US)

(*) Notice: Subject to any disclaimer, the term of this patent is extended or adjusted under 35 U.S.C. 154(b) by 0 days.

(21) Appl. No.: 15/164,159

(22) Filed: May 25, 2016

(65) Prior Publication Data
US 2016/0262618 A1 Sep. 15, 2016

Related U.S. Application Data

(63) Continuation of application No. 14/621,347, filed on Feb. 12, 2015, now Pat. No. 9,380,960, which is a
(Continued)

(51) Int. Cl.
A61B 5/00 (2006.01)
G01R 33/563 (2006.01)
(Continued)

(52) U.S. Cl.
CPC ........... *A61B 5/004* (2013.01); *A61B 5/02007* (2013.01); *A61B 5/0402* (2013.01); *A61B 5/055* (2013.01);
(Continued)

(58) Field of Classification Search
CPC ............ G01R 33/5635; G01R 33/5673; G01R 33/5607; G01R 33/5613; G01R 33/56509; A61B 5/7292; A61B 5/02007; A61B 5/0402; A61B 5/055
See application file for complete search history.

(56) References Cited

U.S. PATENT DOCUMENTS 4,973,906 A 11/1990 Bernstein
5,159,550 A 10/1992 Sakamoto et al.
(Continued)

FOREIGN PATENT DOCUMENTS

WO 2007124244 A1 11/2007

OTHER PUBLICATIONS

Brittain, et al., Three-Dimensional Flow-Independent Peripheral Angiography, Magnetic Resonance in Medicine, 1997, 38:343-354.
(Continued)

Primary Examiner — Bo J Peng
(74) Attorney, Agent, or Firm — Quarles & Brady LLP

(57) ABSTRACT

A method for non-contrast enhanced magnetic resonance angiography ("MRA") that has a short scan time and is insensitive to patient motion is provided. More particularly, the method provides significant arterial conspicuity and substantial venous signal suppression. A two-dimensional single shot acquisition is employed and timed to occur a specific time period after the occurrence of an R-wave in a contemporaneously recorded electrocardiogram. In this manner, k-space data is acquired that is substantially insensitive to variations in arterial flow velocity, or heart rate, and that further substantially suppresses unwanted venous signal in a prescribed imaging slice.

14 Claims, 3 Drawing Sheets

Related U.S. Application Data continuation of application No. 12/574,856, filed on Oct. 7, 2009, now Pat. No. 9,211,081.

(60) Provisional application No. 61/169,925, filed on Apr. 16, 2009.

(51) Int. Cl.

| | |
|---|---|
| *G01R 33/567* | (2006.01) |
| *A61B 5/02* | (2006.01) |
| *A61B 5/0402* | (2006.01) |
| *A61B 5/055* | (2006.01) |
| *G01R 33/56* | (2006.01) |
| *G01R 33/561* | (2006.01) |
| *G01R 33/565* | (2006.01) |

(52) U.S. Cl.
CPC ........... *A61B 5/7285* (2013.01); *A61B 5/7292* (2013.01); *G01R 33/5635* (2013.01); *G01R 33/5673* (2013.01); *G01R 33/5607* (2013.01); *G01R 33/5613* (2013.01); *G01R 33/56509* (2013.01)

(56) References Cited

U.S. PATENT DOCUMENTS

| | | | |
|---|---|---|---|
| 5,492,124 | A | 2/1996 | Purdy |
| 5,652,514 | A | 7/1997 | Zhang et al. |
| 5,999,839 | A | 12/1999 | Hardy et al. |
| 6,240,310 | B1 | 5/2001 | Bundy et al. |
| 6,320,377 | B1 | 11/2001 | Miyazaki et al. |
| 7,412,277 | B1 | 8/2008 | Saranathan et al. |
| 8,332,010 | B2 | 12/2012 | Edelman |
| 9,113,810 | B2 | 8/2015 | Edelman et al. |
| 9,176,212 | B2 | 11/2015 | Edelman |
| 9,211,081 | B2 | 12/2015 | Edelman |
| 9,241,654 | B2 | 1/2016 | Edelman |
| 9,380,960 | B2 | 7/2016 | Edelman |
| 2002/0032376 | A1 | 3/2002 | Miyazaki et al. |
| 2002/0188190 | A1 | 12/2002 | Kassai et al. |
| 2003/0117136 | A1 | 6/2003 | Wang et al. |
| 2005/0010104 | A1 | 1/2005 | Fayad et al. |
| 2005/0065430 | A1 | 3/2005 | Wiethoff et al. |
| 2006/0184002 | A1 | 8/2006 | Yarnykh et al. |
| 2007/0159174 | A1 | 7/2007 | Oshio |
| 2007/0265522 | A1 | 11/2007 | Kassai et al. |
| 2008/0004518 | A1* | 1/2008 | Stehning ................ G01R 33/50 600/410 |
| 2008/0081987 | A1 | 4/2008 | Miyazaki |
| 2009/0062640 | A1 | 3/2009 | Miyoshi |
| 2009/0143666 | A1 | 6/2009 | Edelman et al. |
| 2010/0268062 | A1 | 10/2010 | Edelman |
| 2011/0137146 | A1 | 6/2011 | Edelman |
| 2013/0121550 | A1 | 5/2013 | Chang et al. |
| 2013/0257429 | A1 | 10/2013 | Edelman |
| 2014/0018666 | A1 | 1/2014 | Koktzoglou et al. |
| 2014/0077807 | A1 | 3/2014 | Edelman et al. |
| 2014/0081123 | A1* | 3/2014 | Korosec ............... A61B 5/7285 600/413 |
| 2014/0200435 | A1 | 7/2014 | Edelman et al. |

OTHER PUBLICATIONS

Cukur, et al., Signal Compensation and Compressed Sensing for Magnetization-Prepared MR Angiography, IEEE Transactions on Medical Imaging, 2011, 30(5):1017-1027.
Edelman, et al., Fast Time-of-Flight MR Angiography with Improved Background Suppression, Radiology, 1991, 179:867-870.
Edelman, et al., Unenhanced Flow-Independent MR Venography by Using Signal Targeting Alternative Radiofrequency and Flow-In-dependent Relaxation Enhancement, Radiology, 2009, 250:236-245.
Edelman, et al., Quiescent-Interval Single-Shot Unenhanced Magnetic Resonance Angiography of Peripheral Vascular Disease: Technical Considerations and Clinical Feasibility, Magnetic Resonance in Medicine, 2010, 63 (4):951-958.
Fan, et al., 3D Noncontrast MR Angiography of the Distal Lower Extremities Using Flow-Sensitive Dephasing (FSD)—Prepared Balanced SSFP, Magnetic Resonance in Medicine, 2009, 62:1523-1532.
Fenchel, et al., Multislice First-Pass Myocardial Perfusion Imaging: Comparison of Saturation Recovery (SR)-TrueFISP-Two-Dimensional (2D) and SR-TurboFLASH-2D Pulse Sequences, Journal of Magnetic Resonance Imaging, 2004, 19:555-563.
Francois, et al., Renal Arteries: Isotropic, High-Spatial-Resolution, Unenhanced MR Angiography with Three-Dimensional Radial Phase Contrast, Radiology, 2011, 258(1):254-260.
Gallix, et al., Flow-Independent Magnetic Resonance Venography of the Calf, Journal of Magnetic Resonance Imaging, 2003, 17:421-426.
Hodnett, et al., Evaluation of Peripheral Arterial Disease with Nonenhanced Quiescent-Interval Single-Shot MR Angiography, Radiology, 2011, 260(1):282-293.
Katoh, et al., Free-Breathing Renal MR Angiography with Steady-State Free-Precession (SSFP) and Slab-Selective Spin Inversion: Initial Results, Kidney International, 2004, 66:1272-1278.
Lim, et al., 3D Nongadolinium-Enhanced ECG-Gated MRA of the Distal Lower Extremities: Preliminary Clinical Experience, Journal of Magnetic Resonance Imaging, 2008, 28:181-189.
Lustig, et al., Sparse MRI: The Application of Compressed Sensing for Rapid MR Imaging, Magnetic Resonance in Medicine, 2007,58:1182-1195.
Miyazaki, et al., A Novel MR Angiography Technique: SPEED Acquisition Using Half-Fourier RARE, Journal of Magnetic Resonance Imaging, 1998, 8:505-507.
Miyazaki, et al., Peripheral MR Angiography: Separation of Arteries from Veins with Flow-Spoiled Gradient Pulses in Electrocardiography-Triggered Three-Dimensional Half-Fourier Fast Spin-Echo Imaging, Radiology, 2003, 227:890-896.
Miyazaki, et al., Nonehanced MR Angiography, Radiology, 2008, 248(1):20-43.
Nakamura, et al., Fresh Blood Imaging (FBI) of Peripheral Arteries: Comparison with 16-Detector Row CT Angiography, Proc. Intl. Soc. Mag. Reson. Med., 2006, 14:1929.
Owen, et al., Magnetic Resonance Imaging of Angiographically Occult Runoff Vessels in Peripheral Arterial Occlusive Disease, New England Journal of Medicine, 1992, 326(24):1577-1581.
Scheffler, et al., Reduced Circular Field-Of-View Imaging, Magnetic Resonance in Medicine, 1998, 40:474-480.
Schreiber, et al., Dynamic Contrast-Enhanced Myocardial Perfusion Imaging Using Saturation-Prepared TrueFISP, Journal of Magnetic Resonance Imaging, 2002, 16:641-652.
Wheaton, et al., Non-Contrast Enhanced MR Angiography: Physical Principles, Journal of Magnetic Resonance Imaging, 2012, 36:286-304.
Wright, et al., Flow-Independent Magnetic Resonance Projection Angiography, Magnetic Resonance in Medicine, 1991, 17:126-140.
Xu, et al., A Novel Non-Contrast MR Angiography Technique Using Triggered Non-Selective Refocused SPACE for Improved Spatial Resolution and Speed, Proc. Intl. Soc. Mag. Reson. Med., 2008, 16:730.
Yamada, et al., Visualization of Cerebrospinal Fluid Movement with Spin Labeling at MR Imaging: Preliminary Results in Normal and Pathophysiologic Conditions, Radiology, 2008; 249:644-652.
Yamashita, et al., Selective Visualization of Renal Artery Using SSFP with Time-Spatial Labeling Inversion Pulse: Non-Contrast Enhanced MRA for Patients with Renal Failure, Proc. Intl. Soc. Mag. Reson. Med., 2005, 13:1715.

\* cited by examiner

METHOD FOR NON-CONTRAST ENHANCED MAGNETIC RESONANCE ANGIOGRAPHY

CROSS-REFERENCE TO RELATED APPLICATIONS

This application is a continuation of U.S. application Ser. No. 14/621,347, filed Feb. 12, 2015, and entitled "Method for Non-Contrast Enhanced Magnetic Resonance Angiography," which is a continuation of now issued U.S. Pat. No. 9,211,081 claiming the benefit of U.S. Provisional patent application Ser. No. 61/169,925 filed on Apr. 16, 2009, and entitled "Method for Non-Contrast Enhanced Magnetic Resonance Angiography."

BACKGROUND OF THE INVENTION

The field of the invention is magnetic resonance imaging ("MRI") and systems. More particularly, the invention relates to methods for non-contrast enhanced magnetic resonance angiography ("MRA").

When a substance such as human tissue is subjected to a uniform magnetic field (polarizing field $B_0$), the individual magnetic moments of the nuclei in the tissue attempt to align with this polarizing field, but precess about it in random order at their characteristic Larmor frequency. If the substance, or tissue, is subjected to a magnetic field (excitation field $B_1$) that is in the x-y plane and that is near the Larmor frequency, the net aligned moment, $M_z$, may be rotated, or "tipped", into the x-y plane to produce a net transverse magnetic moment $M_{xy}$. A signal is emitted by the excited nuclei or "spins", after the excitation signal $B_1$ is terminated, and this signal may be received and processed to form an image.

When utilizing these "MR" signals to produce images, magnetic field gradients ($G_x$, $G_y$, and $G_z$) are employed. Typically, the region to be imaged is scanned by a sequence of measurement cycles in which these gradients vary according to the particular localization method being used. The resulting set of received MR signals are digitized and processed to reconstruct the image using one of many well known reconstruction techniques.

The measurement cycle used to acquire each MR signal is performed under the direction of a pulse sequence produced by a pulse sequencer. Clinically available MRI systems store a library of such pulse sequences that can be prescribed to meet the needs of many different clinical applications. Research MRI systems include a library of clinically proven pulse sequences and they also enable the development of new pulse sequences.

Magnetic resonance angiography ("MRA") uses the magnetic resonance phenomenon to produce images of the human vasculature. To enhance the diagnostic capability of MRA, a contrast agent such as gadolinium can be injected into the patient prior to the MRA scan. The trick with this contrast enhanced ("CE") MRA method is to acquire the central k-space views at the moment the bolus of contrast agent is flowing through the vasculature of interest. Collection of the central lines of k-space during peak arterial enhancement, therefore, is key to the success of a CE-MRA exam. If the central lines of k-space are acquired prior to the arrival of contrast, severe image artifacts can limit the diagnostic information in the image. Alternatively, arterial images acquired after the passage of the peak arterial contrast are sometimes obscured by the enhancement of veins. In many anatomic regions, such as the carotid or renal arteries, the separation between arterial and venous enhancement can be as short as 6 seconds.

The short separation time between arterial and venous enhancement dictates the use of acquisition sequences of either low spatial resolution or very short repetition times ("TR"). Short TR acquisition sequences severely limit the signal-to-noise ratio ("SNR") of the acquired images relative to those exams in which a longer TR is employed. The rapid acquisitions required by first pass CE-MRA methods thus impose an upper limit on either spatial or temporal resolution.

Recently, a rare and serious pathology involving fibrosis of skin, joints, eyes, and internal organs referred to as nephrogenic systemic fibrosis ("NSF") has been correlated to the administration of gadolinium-based contrast agents to patients undergoing contrast-enhanced MRA studies. The link between gadolinium-based contrast agents and NSF is described, for example, by P. Marckmann, et al., in "Nephrogenic Systemic Fibrosis: Suspected Causative Role of Gadodiamide Used for Contrast-Enhanced Magnetic Resonance Imaging," *J. Am. Soc. Nephrol.*, 2006; 17 (9):2359-2362. As a result of the increased incidence of NSF, methods for MRA that do not rely on the administration of a contrast agent to the patient have become an important field of research. However, current methods for non-contrast angiography are limited in their utility because they are sensitive to patient motion, do not consistently or accurately portray vessel anatomy in patients with severe vascular disease, and require excessively long scan times.

While single shot acquisition methods such as two-dimensional ("2D") balanced steady-state free precession ("bSSFP") have the potential to reduce motion artifacts and shorten exam times, arterial conspicuity is inadequate due to high background signal. Moreover, bSSFP methods do not lend themselves to the creation of maximum intensity projection ("MIP") angiograms. In one example, a saturation-recovery bSSFP pulse sequence employed for cardiac perfusion imaging following the administration of a paramagnetic contrast agent is described by W. G. Schreiber, et al., in "Dynamic Contrast-Enhanced Myocardial Perfusion Imaging Using Saturation-Prepared TrueFISP," *JMRI*, 2002; 16:641-652. However, this pulse sequence applies a spatially non-selective saturation pulse that suppresses the signal from blood and, thus, cannot be employed for MRA. Additionally, Schreiber's method does not provide a means for distinguishing arteries from veins.

It is, in fact, particularly challenging to suppress venous signal with a single shot acquisition since, unlike arterial blood, venous blood typically flows slowly or even, for periods of time, not at all. In addition, the venous flow pattern is largely unpredictable, sometimes varying with a patient's respiration cycle, cardiac cycle, or both. Consequently, it is problematic to eliminate the signals from veins with single shot acquisitions, since venous blood flows only a short distance or not at all during the short scan time. Unfortunately, venous signals tend to overlap with arterial signals on projection images, thereby making it difficult or impossible to diagnose arterial disease using such methods for MRA. In addition, a robust single shot non-contrast MRA technique must provide an accurate depiction of arterial anatomy over a wide range of flow velocities, ranging from a few centimeters per second ("cm/sec") to more than 100 cm/sec. Moreover, the arterial anatomy must be depicted with sufficient arterial conspicuity to allow creation of a projection angiogram.

Several approaches have been previously described to suppress venous signal on non-contrast MR angiograms as follows. One method for venous suppression has been accomplished using image subtraction. Techniques like fresh blood imaging ("FBI") involve the subtraction of two images with different arterial signals, but identical venous signals. In this manner, the venous, but not arterial, signals cancel with subtraction. Unlike the saturation-based methods, subtraction techniques eliminate the signals from both stationary and moving venous spins. However, image subtraction doubles scan time and greatly increases the sensitivity of the technique to patient motion. In addition, these methods require prior knowledge of flow velocities in order to maximize arterial conspicuity.

Another method for suppressing venous signals is to employ a $T_2$-weighted magnetization preparation pulse, which diminishes signal in veins since venous blood has a reduced oxygen tension. However, this method is inconsistently effective since the level of venous oxygenation varies widely and unpredictably.

Yet another method is to repeatedly apply a saturation radio frequency ("RF") pulse just prior to the pulse sequence used for data acquisition, and to repeat this process multiple times at typical intervals of 20-200 milliseconds ("ms"). However, the use of a single shot acquisition with subsecond data acquisition time does not afford the time to repeatedly apply a saturation RF pulse. As a result, this approach is only applicable to multi-shot acquisition techniques where the data is acquired over tens of seconds to several minutes. Moreover, the repeated application of RF pulses causes marked suppression of arterial signal in tortuous vessels, thereby limiting the diagnostic accuracy of these methods.

A single shot acquisition method for MRA is described by R. Edelman, et al., in "Fast Time-of-Flight MR Angiography with Improved Background Suppression," *Radiology*, 1991; 179:867-870. This method requires the use of an inversion recovery preparation pulse and relies on arterial inflow during the data acquisition period to produce arterial contrast. In this respect, the inversion time ("TI") is selected solely to match the center lines of k-space to the "null" point for the longitudinal magnetization of background tissue, and is not selected in order to allow for the inflow of arterial blood into the imaging slice. In other words, the purpose of the TI is to reduce the signal intensity of background tissues.

This method suffers from several drawbacks. For example, the method acquires data over a lengthy time period on the order of one second, thereby encompassing both systole and diastole. With this lengthy time period required for data acquisition, it is not possible to synchronize TI to the period of rapid, systolic arterial flow, nor to the period of slow diastolic flow. Moreover, the TI employed by Edelman is too short (on the order of 75 ms) to allow for substantial arterial inflow. As a result, most of the arterial inflow occurs during the application of repeated RF pulses. As described above, the repeated application of RF pulses in this manner causes marked suppression of arterial signal in tortuous vessels, thereby limiting the diagnostic accuracy of such methods for MRA. The method also does not allow for the effective suppression of venous or fat signals, which are both essential to accurately depict the arteries.

Other methods of non-contrast enhanced MRA are described, for example, by M. Katoh, et al., in "Free-Breathing Renal MR Angiography With Steady-State Free-Precession (SSFP) and Slab-Selective Spin Inversion: Initial Results," *Kidney International*, 2004; 66:1272-1278, and by Y. Yamashita, et al., in "Selective Visualization of Renal Artery Using SSFP with Time-Spatial Labeling Inversion Pulse: Non-Contrast Enhanced MRA for Patients with Renal Failure," *Proc. Intl. Soc. Mag. Reson. Med.* 13 (2005) p. 1715. The method described by Katoh utilizes a three-dimensional ("3D") acquisition with a pre-inversion of the 3D region, while Yamashita employs two inversion pulses (one spatially selective and the other spatially non-selective). Each of these methods uses inversion preparation pulses rather than saturation pulses and further requires the use of a 3D, rather than 2D, acquisition for MRA. Given the substantial thickness of the 3D imaging slab, inflowing unsaturated spins must travel a large distance (for example, up to several centimeters) to replace in-plane saturated ones. Consequently, there is poor depiction of slowly flowing arterial spins. In fact, the inversion time, TI, must be very long (on the order of 1 second) to provide adequate inflow of even moderately fast flowing arterial spins. The long TI spans both the systolic and diastolic phases of the cardiac cycle. Given the long TI, it is problematic to synchronize data acquisition to diastole. In addition, 3D acquisitions are too time-consuming to permit data acquisition within a single breath-holding period.

A 2D adaptation of Yamashita's "time-SLIP" acquisition is described by S. Yamada, et al., in "Visualization of Cerebrospinal Fluid Movement with Spin Labeling at MR Imaging: Preliminary Results in Normal and Pathophysiologic Conditions," *Radiology*, 2008; 249;644-652. This method, however, is employed to image the flow of cerebrospinal fluid flow rather than for MRA applications. Additionally, it uses two inversion pulses, rather than saturation pulses, and has a very long TI (on the order of 2500 ms) that is incompatible with MRA studies.

It would therefore be desirable to provide a method for non-contrast enhanced MRA that produced images of a patient's vasculature in a relatively short duration of time while maintaining significant discrimination of the arteries and substantially suppressing venous signals. Moreover, it would be desirable to provide a method for non-contrast enhanced MRA that was insensitive to flow velocities and was relatively insensitive to patient motion and other imaging artifacts.

SUMMARY OF THE INVENTION

The present invention overcomes the aforementioned drawbacks by providing a method for non-contrast enhanced magnetic resonance angiography ("MRA") that has a short scan time and is insensitive to patient motion, while maintaining significant arterial conspicuity and substantial venous signal suppression. This is achieved by employing a two-dimensional ("2D") single shot acquisition.

It is an aspect of the invention to provide a method for non-contrast enhanced MRA that is substantially insensitive to variations in arterial flow velocity or heart rate and that further substantially suppresses unwanted venous signal in a prescribed 2D imaging slice. A method for accurately depicting normal and diseased arteries despite a wide range of flow velocities is provided by synchronizing a quiescent interval ("QI") to the period of rapid, systolic arterial blood flow so as to maximize flow-related enhancement into the imaging slice. Additionally, this method is provided by synchronizing data acquisition to occur during diastole when arterial blood is stationary or flowing relatively slowly into a prescribed imaging slice. If venous blood flow is flowing in a cranial direction and arterial blood flow in a caudal direction, as is the case for the peripheral arteries, this venous suppression can be further augmented by the application of saturation pulses prior to the QI. The saturation pulses are applied not only in the imaging slice, but also in a slab contiguous with and caudal to the imaging slice.

Likewise, when venous blood is flowing in a caudal direction and arterial blood in the cranial direction, as is the case in the internal jugular vein and common carotid artery, respectively, the slab is selected to be contiguous with and cranial to the imaging slice. In this manner, saturated venous spins and unsaturated arterial spins will flow into the imaging slice over the duration of the QI. Such a method differs fundamentally from previously described methods for suppressing venous signal since, in prior methods, saturation pulses were applied directly before the radio frequency ("RF") excitation, allowing negligible time for inflow of saturated venous spins into the imaging slice.

It is another aspect of the invention to provide a method for non-contrast enhanced MRA that can produce images in a relatively short duration of time. For example, the entire length of the peripheral arteries can be imaged in 8 minutes with high arterial conspicuity and marked suppression of venous signal. Since the method uses a single shot acquisition, no ghost artifacts occur and the method is highly resistant to motion artifact. Previously described MRA techniques, including fresh blood imaging and 2D time of flight, do not use a single shot acquisition and thus are prone to motion artifacts and longer scan times. Additionally, the shortened scan time required with the method of the present invention allows for a series of 2D images to be obtained within a single breath-hold.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Figure 1:
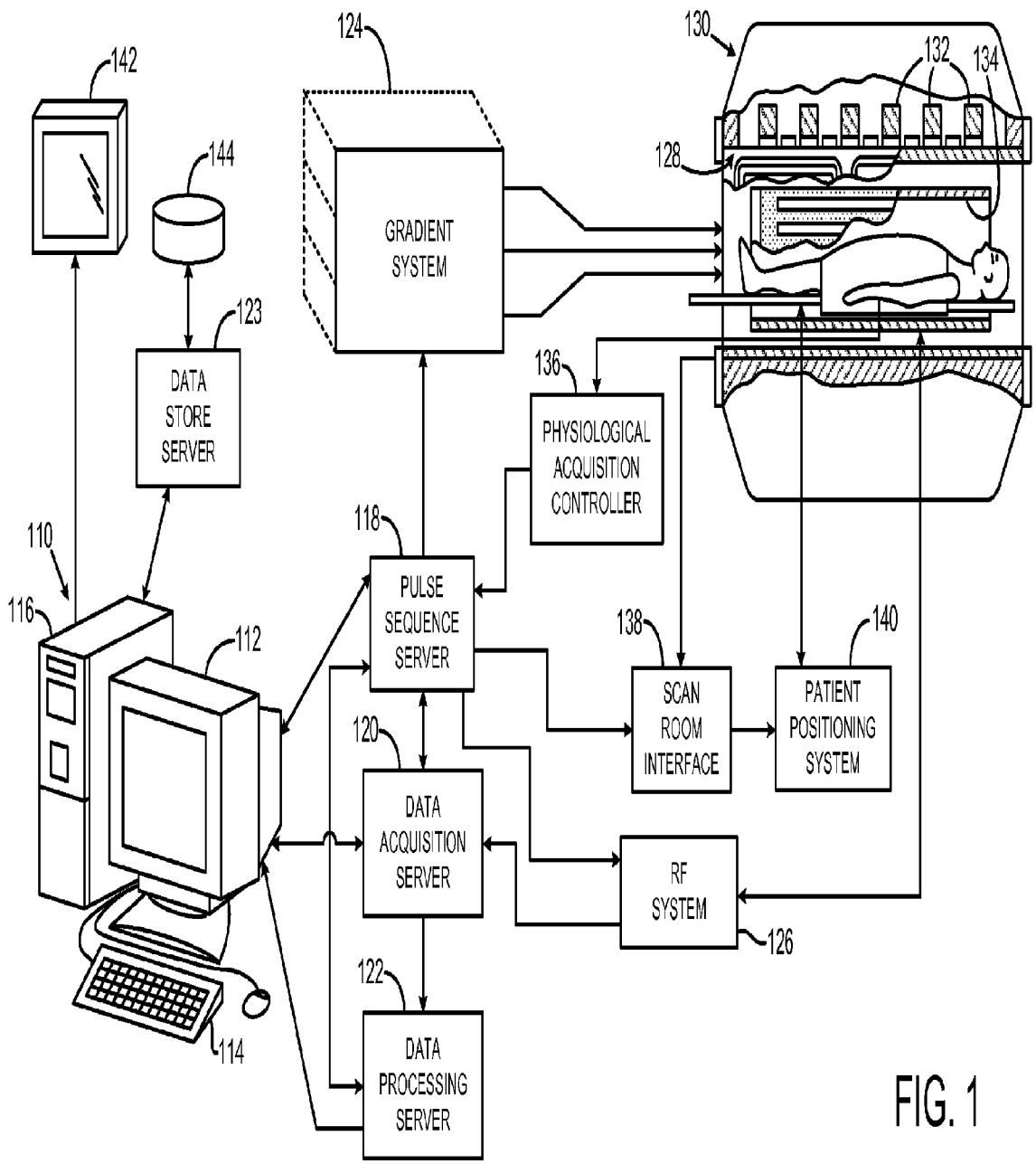
FIG. 1 is a block diagram of an MRI system that employs the present invention.

Referring particularly to FIG. 1, the preferred embodiment of the invention is employed in an MRI system. The MRI system includes a workstation 110 having a display 112 and a keyboard 114. The workstation 110 includes a processor 116 that is a commercially available programmable machine running a commercially available operating system. The workstation 110 provides the operator interface that enables scan prescriptions to be entered into the MRI system. The workstation 110 is coupled to four servers: a pulse sequence server 118; a data acquisition server 120; a data processing server 122, and a data store server 123. The workstation 110 and each server 118, 120, 122 and 123 are connected to communicate with each other.

The pulse sequence server 118 functions in response to instructions downloaded from the workstation 110 to operate a gradient system 124 and a radio frequency ("RF") system 126. Gradient waveforms necessary to perform the prescribed scan are produced and applied to the gradient system 124 that excites gradient coils in an assembly 128 to produce the magnetic field gradients $G_x$, $G_y$, and $G_z$ used for position encoding MR signals. The gradient coil assembly 128 forms part of a magnet assembly 130 that includes a polarizing magnet 132 and a whole-body RF coil 134.

RF excitation waveforms are applied to the RF coil 134 by the RF system 126 to perform the prescribed magnetic resonance pulse sequence. Responsive MR signals detected by the RF coil 134 or a separate local coil (not shown in FIG. 1) are received by the RF system 126, amplified, demodulated, filtered and digitized under direction of commands produced by the pulse sequence server 118. The RF system 126 includes an RF transmitter for producing a wide variety of RF pulses used in MR pulse sequences. The RF transmitter is responsive to the scan prescription and direction from the pulse sequence server 118 to produce RF pulses of the desired frequency, phase and pulse amplitude waveform. The generated RF pulses may be applied to the whole body RF coil 134 or to one or more local coils or coil arrays (not shown in FIG. 1).

The RF system 126 also includes one or more RF receiver channels. Each RF receiver channel includes an RF amplifier that amplifies the MR signal received by the coil to which it is connected and a detector that detects and digitizes the I and Q quadrature components of the received MR signal. The magnitude of the received MR signal may thus be determined at any sampled point by the square root of the sum of the squares of the I and Q components:

$$M=\sqrt{I^2+Q^2},$$

and the phase of the received MR signal may also be determined:

$$\phi = \tan^{-1}\left(\frac{Q}{I}\right).$$

The pulse sequence server 118 also optionally receives patient data from a physiological acquisition controller 136. The controller 136 receives signals from a number of different sensors connected to the patient, such as ECG signals from electrodes or respiratory signals from a bellows. Such signals are typically used by the pulse sequence server 118 to synchronize, or "gate", the performance of the scan with the subject's respiration or heart beat.

The pulse sequence server 118 also connects to a scan room interface circuit 138 that receives signals from various sensors associated with the condition of the patient and the magnet system. It is also through the scan room interface circuit 138 that a patient positioning system 140 receives commands to move the patient to desired positions during the scan.

The digitized MR signal samples produced by the RF system 126 are received by the data acquisition server 120. The data acquisition server 120 operates in response to instructions downloaded from the workstation 110 to receive the real-time MR data and provide buffer storage such that no data is lost by data overrun. In some scans the data acquisition server 120 does little more than pass the acquired MR data to the data processor server 122. However, in scans that require information derived from acquired MR data to control the further performance of the scan, the data acquisition server 120 is programmed to produce such information and convey it to the pulse sequence server 118. For example, during prescans MR data is acquired and used to calibrate the pulse sequence performed by the pulse sequence server 118. Also, navigator signals may be acquired during a scan and used to adjust RF or gradient system operating parameters or to control the view order in which k-space is sampled. And, the data acquisition server 120 may be employed to process MR signals used to detect the arrival of contrast agent in a magnetic resonance angiography (MRA) scan. In all these examples the data acquisition server 120 acquires MR data and processes it in real-time to produce information that is used to control the scan.

The data processing server 122 receives MR data from the data acquisition server 120 and processes it in accordance with instructions downloaded from the workstation 110. Such processing may include, for example: Fourier transformation of raw k-space MR data to produce two or three-dimensional images; the application of filters to a reconstructed image; the performance of a backprojection image reconstruction of acquired MR data; the calculation of functional MR images; the calculation of motion or flow images, etc.

Images reconstructed by the data processing server 122 are conveyed back to the workstation 110 where they are stored. Real-time images are stored in a data base memory cache (not shown) from which they may be output to operator display 112 or a display 142 that is located near the magnet assembly 130 for use by attending physicians. Batch mode images or selected real time images are stored in a host database on disc storage 144. When such images have been reconstructed and transferred to storage, the data processing server 122 notifies the data store server 123 on the workstation 110. The workstation 110 may be used by an operator to archive the images, produce films, or send the images via a network to other facilities.

Figure 2:
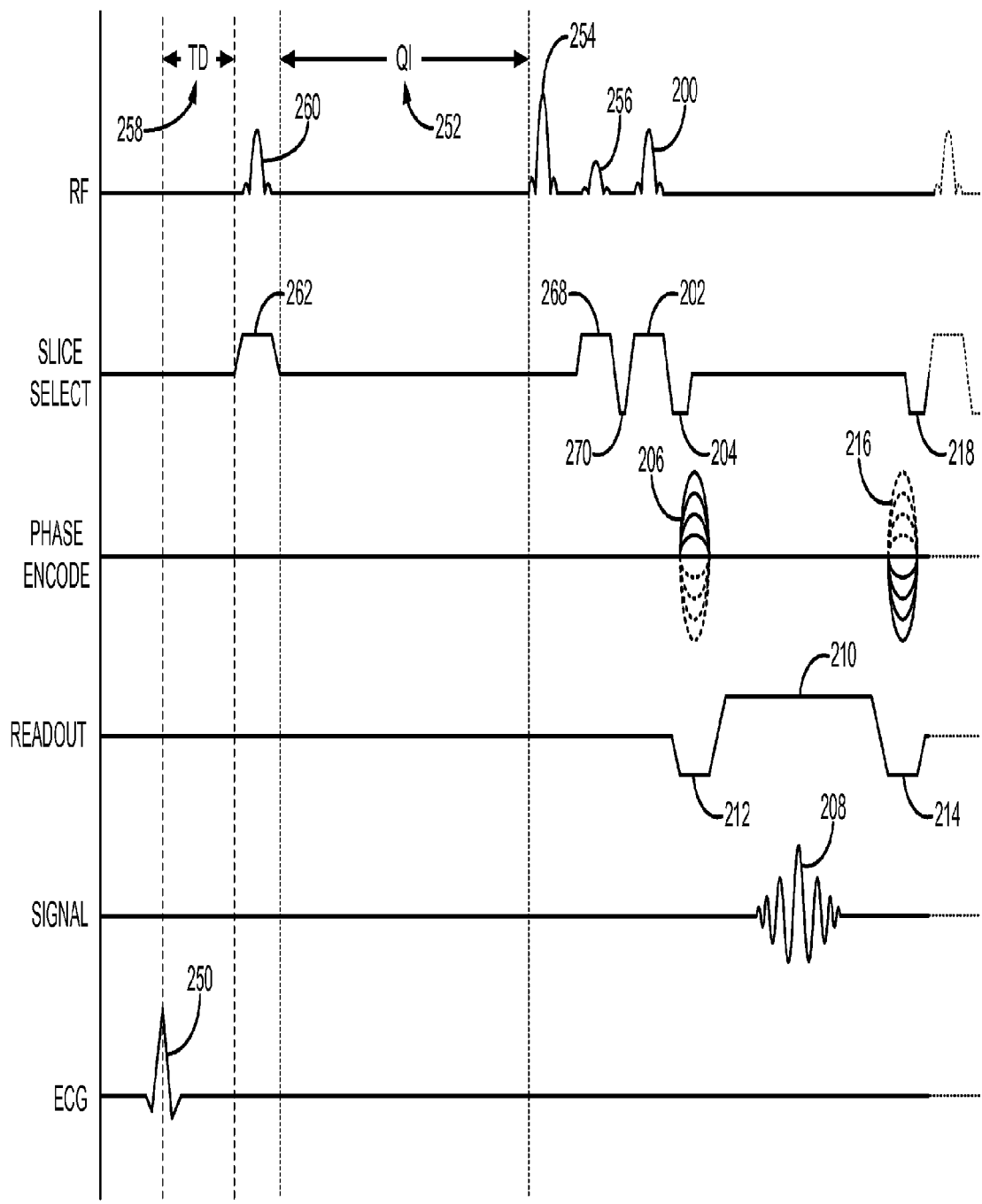
FIG. 2 is a pictorial representation of a pulse sequence performed by the MRI system of FIG. 1 when practicing an embodiment the present invention.

Referring now particularly to FIG. 2, a pulse sequence employed when practicing an embodiment of the present invention is pictorially shown. The pulse sequence is cardiac gated, such that the acquisition of k-space data is timed with respect to the flow of arterial blood. Specifically, the pulse sequence is timed to be played out with respect to the peak of the R-wave 250 in a concurrently acquired echocardiogram ("ECG"). It should be appreciated by those skilled in the art, however, that other methods for cardiac synchronization of the following pulse than relying on an ECG signal are possible. For example, cardiac synchronization can be achieved using self-gating techniques that rely on measurement of flow signal or phase. Turning now to the pulse sequence, a slice-selective RF saturation pulse 260 is first played out in the presence of a slice-selective gradient 262 The application of this slice-selective RF saturation pulse 260 has the effect of suppressing the signals from background tissues as well as those venous spins that are present in the prescribed slice. The flip angle for this slice-selective RF saturation pulse 260 is typically about 90 degrees; however, larger or smaller flip angles may be desirable in some circumstances. The slice-selective RF saturation pulse 260 is timed to occur at a preset time delay ("TD") after the occurrence of the R-wave 250. For example, TD is set to 100 ms.

The duration of time that is allowed to pass after the application of the slice-selective RF saturation pulse 260 is herein referred to as the "quiescent interval" ("QI"). This duration of time is specifically tailored to coincide with the rapid inflow of arterial blood into a prescribed imaging slice, and so that the zero line of k-space is acquired during the slow, diastolic inflow of arterial blood into the imaging slice. More particularly, a central portion of k-space is sampled during the slow, diastolic inflow of arterial blood into the imaging slice before the peripheral regions of k-space are sampled. The result of this is a substantial suppression of flow-based image artifacts. Put another way, this provides a method that is substantially insensitive to flow velocities in the prescribed image slice. Moreover, the QI allows for a maximal inflow of unsaturated arterial spins into the imaging slice, such that an improved discrimination of arterial spins is provided in the resultant images. This is even so when the patient's vasculature is significantly impacted by vascular diseases such as peripheral vascular disease ("PVD"). Exemplary values of QI in this configuration of the pulse sequence are on the order of 260 ms.

After the QI has passed, the pulse sequence proceeds with data acquisition, which is accomplished, for example, with a single shot balanced steady-state free procession (SSFP) gradient echo pulse sequence. First, a spectrally selective fat saturation RF pulse 254 is applied to further suppress unwanted MR signals originating from fat tissue. This is subsequently followed by a slice-selective α/2 magnetization RF pulse 256 that is played out in the presence of a slice-selective gradient 268, where a is a user selected flip angle. The slice-selective gradient includes a rephasing lobe 270 that acts to mitigate unwanted phase accruals that occur during the application of the slice-selective gradient 268. This portion of the pulse sequence includes a slice-selective RF excitation pulse 200 that is played out in the presence of a slice-selective gradient pulse 202 to produce transverse magnetization in a prescribed slice. The slice-selective gradient includes a rephasing lobe 204 that acts to mitigate unwanted phase accruals that occur during the application of the slice-selective gradient 202. After excitation of the spins in the slice, a phase encoding gradient pulse 206 is applied to position encode the MR signal 208 along one direction in the slice. A readout gradient pulse 210 is also applied after a dephasing gradient lobe 212 to position encode the MR signal 206 along a second, orthogonal direction in the slice. Like the slice-selective gradient 202, the readout gradient 210 also includes a rephasing lobe 214 that acts to mitigate unwanted phase accruals.

To maintain the steady state condition, the integrals along the three gradients each sum to zero during the repetition time ("TR") period. To accomplish this, a rewinder gradient lobe 216 that is equal in amplitude, but opposite in polarity of the phase encoding gradient 206, is played out along the phase encoding gradient axis. Likewise, a dephasing lobe 218 is added to the slice select gradient axis, such that the dephasing lobe 218 precedes the repetition of the slice-selective gradient 202 in the next TR period. As is well known in the art, the reading out of MR signals following the single shot of the RF excitation pulse 200 is repeated and the amplitude of the phase encoding gradient 206 and its equal, but opposite rewinder 216 are stepped through a set of values to sample 2D k-space in a prescribed manner. It should be appreciated by those skilled in the art that any number of data acquisition schemes can be employed to acquire k-space data instead of balanced SSFP. For example, spoiled gradient echo, spiral acquisition, or echo planar imaging ("EPI") pulse sequences can alternatively be utilized.

Figure 3:
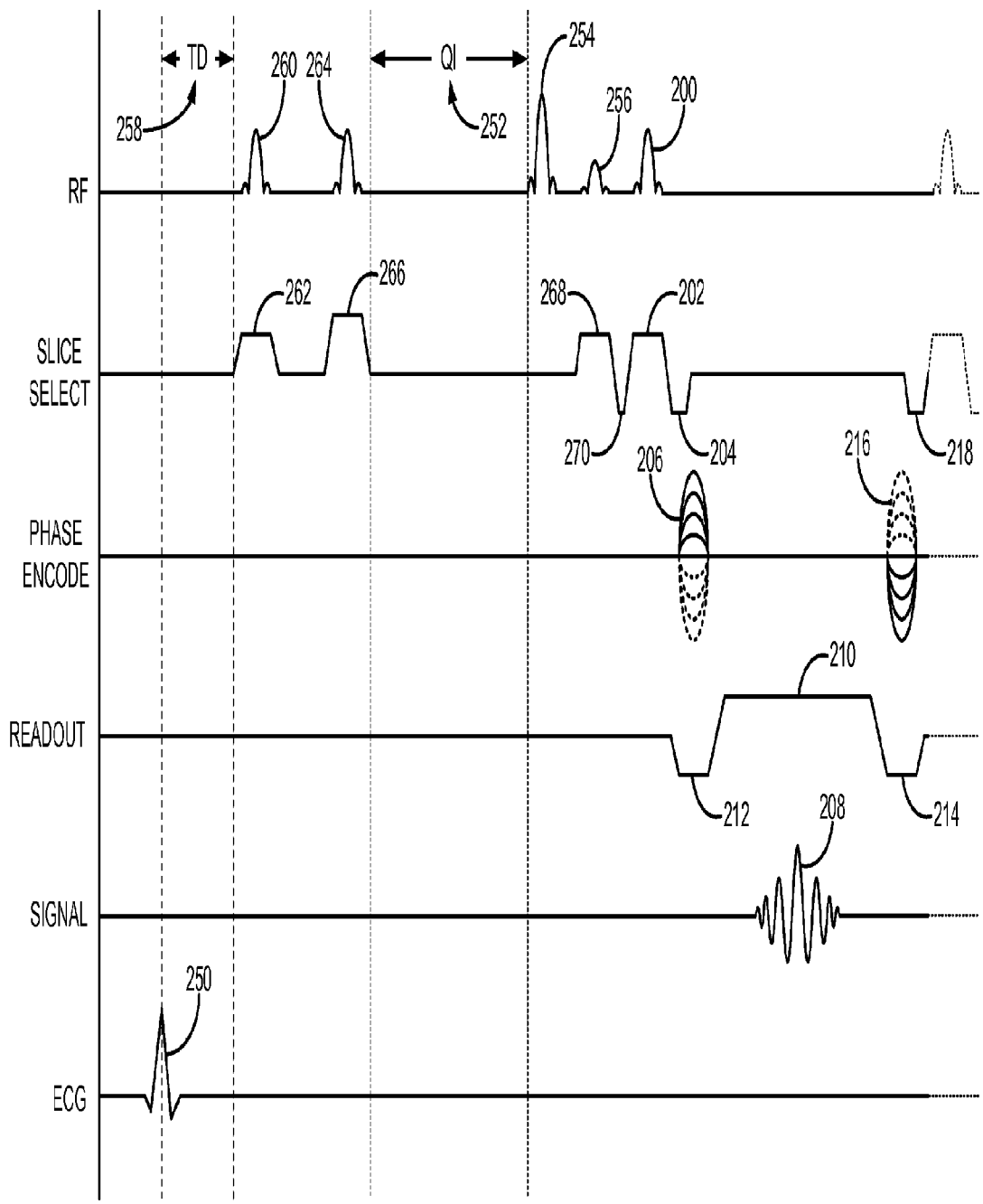
FIG. 3 is a pictorial representation of a pulse sequence performed by the MRI system of FIG. 1 when practicing another embodiment the present invention.

Referring now particularly to FIG. 3, another configuration of the pulse sequence employed when practicing the present invention is pictorially shown. This pulse sequence is also cardiac gated, such that the acquisition of k-space data is timed with respect to the flow of arterial blood. Specifically, the pulse sequence is timed to be played out with respect to the peak of the R-wave 250 in a concurrently acquired echocardiogram ("ECG"). However, the data acquisition portion of the pulse sequence is preceded by the application of two RF saturation pulses. By employing RF saturation pulses instead of inversion recovery pulses, the longitudinal magnetization is always reset to zero prior to the beginning of the QI. This is not necessarily the case when employing inversion recovery-based methods, as residual longitudinal magnetization resulting from inadequate inversion may confound the subsequently detected MR signals. Moreover, by always resetting the longitudinal magnetization of the slice to zero, the use of a slice-selective RF saturation pulse ensures that the tissue signal remains substantially uniform across different slices despite variations in the R-R interval due to cardiac arrhythmias. This is not the case with inversion-recovery based methods.

First, a slice-selective RF saturation pulse 260 is played out in the presence of a slice-selective gradient 262. The application of this slice-selective RF saturation pulse 260 has the effect of suppressing the signals from background tissues as well as those venous spins that are present in the prescribed slice. The slice-selective RF saturation pulse 260 is timed to occur at a preset time delay ("TD") after the occurrence of the R-wave 250. For example, TD is set to 100 ms.

To suppress signals from venous spins that will flow into the prescribed slice, a second, slab-selective RF saturation pulse 264 is played out in the presence of a slab-selective gradient 266. The slab-selective RF saturation pulse 264 has the effect of suppressing venous signals in a slab that is contiguous with the prescribed imaging slice. Specifically, when imaging the peripheral arteries, the prescribed slab is chosen to be caudal to, and contiguous with, the prescribed imaging slice such that saturated venous blood flows into the imaging slice in the caudal-cranial direction while unsaturated arterial spins flow into the imaging slice in the cranial-caudal direction. Similarly, when imaging, for example, the carotid artery, the prescribed slab is chosen to be cranial to, and contiguous with, the prescribed imaging slice such that saturated venous blood flows into the imaging slice in the cranial-caudal direction while unsaturated arterial spins flow into the imaging slice in the caudal-cranial direction. Exemplary RF excitation slab thicknesses are on the order of 150 mm; however, it will be appreciated by those skilled in the art that other thicknesses can be selected depending on the intended application and subject at hand. It will also be appreciated that in some circumstances it may be desirable to shift the RF excitation slab so that it is not contiguous with the imaging slice.

In this alternate configuration of the pulse sequence, the QI is defined as the duration of time occurring after the application of the slab-selective RF saturation pulse 264 and before the fat saturation pulse 254. Like the previously described QI, however, this duration of time is specifically tailored so that the zero line of k-space is acquired during the slow, diastolic inflow of arterial blood into the prescribed imaging slice. As described above, the result of allowing the QI to pass before data acquisition is a substantial suppression of flow-based image artifacts. Put another way, this provides a method that is substantially insensitive to flow velocities in the prescribed image slice. Exemplary values of QI in this configuration of the pulse sequence are on the order of 250 ms. The proceeding data acquisition is played out similar to the above-described pulse sequence, which is so described with respect to FIG. 2.

Unlike previous methods that rely on multi-shot acquisitions, the repetition time of the pulse sequences employed when practicing the present invention are significantly shorter than, say, the 30 ms typically required of such multi-shot sequences. In this manner, the overall scan time is less than the several seconds required of previous methods. This allows the method of the present invention to acquire the desired image data without becoming significantly sensitive to subject motion. Additionally, the shortened data acquisition period provided by the present invention allows image data to be acquired during only a portion of arterial flow, such that variations in flow velocity during the cardiac cycle do not confound the acquired MR signals.

The present invention has been described in terms of one or more preferred embodiments, and it should be appreciated that many equivalents, alternatives, variations, and modifications, aside from those expressly stated, are possible and within the scope of the invention. For example, it should be appreciated by those skilled in the art that a plurality of different saturation pulses may be employed prior to the beginning of the QI, with an appropriate change in QI. For example, as more saturation pulses are added, QI may decrease down to about 100 ms. Additionally, the specific order of the RF saturation pulses can be altered, such that a slab-selective saturation pulse is applied prior to a slice-selective saturation pulse, without significantly changing the resultant image contrast.

The invention claimed is:

1. A method for non-contrast-enhanced magnetic resonance angiography for imaging the vasculature of a subject with the steps comprising:
   a) directing a magnetic resonance imaging (MRI) system to perform a pulse sequence timed using an acquired trigger signal, the pulse sequence comprising:
      i) a radio frequency (RF) saturation pulse applied to an imaging slice such that MR signals therein are suppressed, the RF saturation pulse being applied at a time point determined based on the acquired trigger signal;
      ii) a quiescent interval, in which no RF pulses are applied to the imaging slice, that is sufficient in duration to allow spins associated with unsaturated blood to flow into the imaging slice;
      iii) a data acquisition that is synchronized to a diastolic period of the cardiac cycle; and
   b) reconstructing, using k-space data acquired in the data acquisition, an image of the subject that is representative of the vasculature of a subject.

2. The method as recited in claim 1, wherein the acquired trigger signal is derived from an electrocardiogram.

3. The method as recited in claim 1, wherein the acquired trigger signal is derived from signal changes within a cardiac or vascular structure.

4. The method as recited in claim 1 in which step a)iii) includes acquiring k-space data as a single shot or multi-shot in coordination with the application of a series of RF excitation pulses.

5. The method as recited in claim 4, wherein a central portion of k-space is sampled during the diastolic inflow before a peripheral portion of k-space is sampled.

6. The method as recited in claim 4 in which step a)iv) includes acquiring k-space data from a zero-line in k-space using zero phase-encoding before acquiring k-space data from the remainder of k-space.

7. The method as recited in claim 1 comprising repeating step a) to acquire another k-space data.

8. The method as recited in claim 7 in which the another k-space data is acquired for a different imaging slice.

9. The method as recited in claim 8 in which the another k-space data is used to reconstruct another image.

10. The method as recited in claim 1 in which the pulse sequence further comprises waiting for a period of time before performing step a)i).

11. The method as recited in claim 10 in which the period of time is between 0 and 150 milliseconds.

12. The method as recited in claim 1 in which the pulse sequence comprises at least one RF saturation pulse applied to a prescribed slab that is outside of the imaging slice, such that MR signals indicative of either venous or arterial blood flowing into the imaging slice are suppressed.

13. The method as recited in claim 1 in which k-space data is acquired from outside the imaging slice during the quiescent interval.

14. The method as recited in claim 1 in which the saturation pulse has a flip angle of 90 degrees.

* * * * *

UNITED STATES PATENT AND TRADEMARK OFFICE
CERTIFICATE OF CORRECTION

PATENT NO. : 9,526,423 B2  
APPLICATION NO. : 15/164159  
DATED : December 27, 2016  
INVENTOR(S) : Robert Edelman Page 1 of 1

It is certified that error appears in the above-identified patent and that said Letters Patent is hereby corrected as shown below:

In the Claims

Claim 6, Column 10, Line 58, change "a)iv" to --a)iii--.

Signed and Sealed this  
Ninth Day of May, 2017

Michelle K. Lee  
*Director of the United States Patent and Trademark Office*